United States Patent
Hirt et al.

(10) Patent No.: US 6,862,085 B2
(45) Date of Patent: Mar. 1, 2005

(54) DEVICE FOR DETECTING TRANSMISSION LOSSES BY MEANS OF MEASUREMENTS

(75) Inventors: Joachim Hirt, Constance (DE); Thomas Glenzer, Kreuzlingen (CH); Armin Kamp, Radolfzell (DE)

(73) Assignee: Ferton Holding S.A., Delemont (CH)

(*) Notice: Subject to any disclaimer, the term of this patent is extended or adjusted under 35 U.S.C. 154(b) by 151 days.

(21) Appl. No.: 10/181,054

(22) PCT Filed: Nov. 29, 2000

(86) PCT No.: PCT/EP00/11930

§ 371 (c)(1),
(2), (4) Date: Oct. 1, 2002

(87) PCT Pub. No.: WO01/51905

PCT Pub. Date: Jul. 19, 2001

(65) Prior Publication Data

US 2003/0107726 A1 Jun. 12, 2003

(30) Foreign Application Priority Data

Jan. 14, 2000 (DE) ........................................ 100 01 289

(51) Int. Cl.$^7$ ............................................. G01N 21/00
(52) U.S. Cl. .................................................... 356/73.1
(58) Field of Search ........................ 356/73.1; 385/115, 385/141; 156/275.5, 275.7, 244.12; 600/180, 431, 473; 250/372, 373, 228, 504 R

(56) References Cited

U.S. PATENT DOCUMENTS 5,268,732 A * 12/1993 Sato ........................... 356/73.1

FOREIGN PATENT DOCUMENTS

| DE | 35 15612 A1 | 11/1985 |
| DE | 43 25 671 A1 | 2/1995 |
| EP | 0 416 408 A2 | 8/1990 |
| GB | 1 532 423 | * 11/1978 |

* cited by examiner

Primary Examiner—Tu T. Nguyen
(74) Attorney, Agent, or Firm—Diller, Ramik & Wight

(57) ABSTRACT

In a device for detecting transmission losses of optical light guide means (2) of an endoscope (3) by means of measurements, said optical light guide means (2) having an optical inlet portion (4) through which light from a light source (6) is transmitted to an optical outlet portion (8) of the means to be checked, said device comprising at least one light sensor (10) measuring the light intensity emerging from the optical outlet portion (8) of the means (2) to be checked, and an evaluation means (14) for the signal of the at least one light sensor (10), said evaluation means (14) having a display means (18) for displaying the measurement result, it is provided that the at least one light sensor (10) is arranged in a chamber (20), that the optical outlet portion (8) of the light guide means (2) to be checked is adapted to be introduced through an opening (22) of the chamber (20) into the chamber (20), and that the inner surface (24) defining the chamber (20) diffusely reflects the light emerging from the optical outlet portion (8).

13 Claims, 1 Drawing Sheet

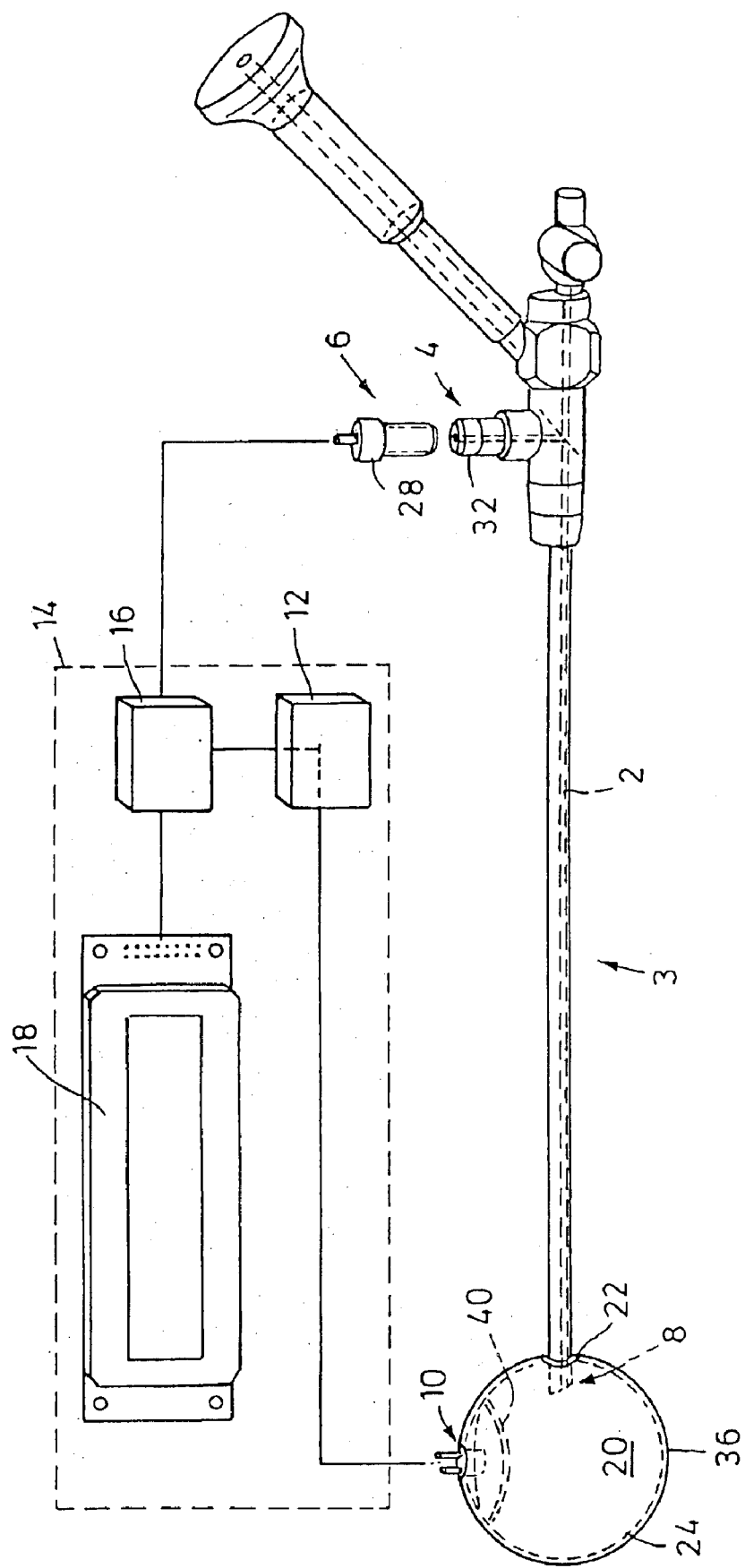

DEVICE FOR DETECTING TRANSMISSION LOSSES BY MEANS OF MEASUREMENTS

BACKGROUND OF THE INVENTION

The invention relates to a device for detecting transmission losses of optical light guide means of an endoscope by means of measurements.

An examination of endoscopes and associated light guide cables has frequently shown that the light guide means suffer high transmission losses. Due to mechanical stress, such as bending and winding-up of the light guide cable, tensile stresses when a light guide cable is strongly pulled, bending of the endoscope shaft, and thermal stress during hot-steam sterilization, individual fibers of the light guide means may break. Frequently, there are deposits on the optical inlet and outlet surfaces of the optical inlet and outlet portions. These deficiencies do normally not lead to an immediate failure of the overall illumination means but to a progressive deterioration of the transmission. Owing to the gradual transition to higher transmission losses the deterioration of the illumination intensity is frequently detected too late. If the surgeon notes during an operation that the endoscope used cannot adequately illuminate the operating area, he has to stop the operation in most cases since there is no further sterilized endoscope available to him.

It would therefore be necessary to check the endoscopic instruments prior to their use.

Instruments for determining various photometric measured variables are known. These instruments use an optical sensor for detecting the light emerging from the light source via the light guide means.

DE 35 15 612 A discloses a light source instrument for an endoscope with a checking means for the light source. An examination the light guide cables or an endoscope is not intended.

In DE 43 25 671 A a method and a device for measuring the damping effect in light wave guides using a pulsed light transmitter is disclosed. The transmitter signal is subjected to a pulse frequency modulation with the aid of which variations in the output power are eliminated. This measuring method is very exact but too complex for quickly checking light guide means in operating theaters.

From EP 0 416 408 A a checking means is known where the light source of the endoscopic means comprises a beam splitter in the beam path. A portion of the light beam is directed to a first sensor, while the other portion is directed via a light guide cable to be checked to a second sensor. By comparing the measured values of the first and the second sensor the transmittance is determined. It is of disadvantage that two light sensors are required which may have different sensitivities and thus have to be calibrated. Splitting of the light beam with the aid of a beam splitter also requires careful calibration. The checking means does not possess its own light source and therefore depends on the light source of the endoscopic means such that additional brightness limit values must be fixed to assess the light intensity of the light source. It is disadvantageous that the checking means is integrated into an existing endoscopic equipment and cannot be generally used for checking light guide means of an endoscope. In particular, the known means allows only light guide cables or the lamp of the light source of a specific means to be checked, but not the endoscope proper.

SUMMARY OF THE INVENTION

It is therefore an object of the invention to provide a device for detecting transmission losses of optical light guide means of an endoscope by measurements, said device allowing rapid checking of different light guide means independent of the light source of the endoscopic means.

This object is achieved with the features of claim 1.

The invention advantageously provides that the least one light sensor is arranged in a chamber, that the optical outlet portion of the light guide means to be checked is adapted to be introduced through an opening in the chamber into the chamber, and that the inner surface defining the chamber diffusely reflects the light emerging from the optical outlet portion of the means to be checked.

The arrangement of the light sensor in a diffusely reflecting chamber offers the advantage that the light emerging from the means to be checked can be detected to a large extent independent of its direction and its input cross-section. It is therefore possible to check different light guide means of different manufacturers for their transmission losses. Even the light guide means of endoscopes can be checked without large expenditure and with a high degree of reproducibility of the measured values. The entry of extraneous light at the opening of the chamber is reliably prevented, e.g. with the aid of one or a plurality of flexible seals. The device according to the invention is universally usable, independent of the endoscopic means, and is suitable for quickly examining light guide means prior to an operation. In particular, it is no longer necessary to return an endoscope to the manufacturer for the purpose of examining its transmission losses.

Preferably, it is provided that a separate light source, which is independent of the means to be checked, couples a predetermined light intensity into the optical inlet portion of the light guide means to be checked. The employment of a separate light source offers the advantage that a defined predetermined light intensity can be used for checking purposes without a recalibration of reference values having to be performed for each check. Endoscopic means normally use halogen lamps or gas-discharge lamps. These light sources possess a high radiation power and are mostly controlled such that the adjustment of a reproducible and constant light intensity is difficult. Further, these light sources are subject to an ageing process such that fixed control values also need to be recalibrated. In contrast to this, a constant light intensity can be assumed when an independent checking light source is used which must not be permanently calibrated.

Particulary advantageous is the use of a light-emitting diode as a light source. Since the measurement of the transmission losses does not require high light intensities, it is possible to employ a light-emitting diode. Said diode is inexpensive and can be adjusted by constant-current control to an adequate and highly reproducible light intensity. Calbration is thus not necessary since a fixed and stored reference value can be used for the light source which is solely employed for checking purposes.

According to preferred aspect of the invention the light source is arranged in a connector adapted to standardized connections of the optical inlet portion of the means to be checked. The connector adapted to the standardized connections allows the light source to be quickly connected to the inlet side of the light-conducting means and reliable seating on the means to be checked.

According to a preferred aspect the inner surface of the chamber is of spherical configuration. It is of importance for the measurig accuracy that the entire transmitted light is detected and evaluated. Endoscopes illuminate e.g. the place of observation at differently large aperture angles depending on the embodiment and the application. Further, the light can emerge from the light guide means at an angle relative to the instrument axis. The chamber defined by a spherical inner surface is capable of diffusely reflecting the entire light emerging from the optical outlet portion independent of the radiation angle and the diameter of the light exit such that the at least one light sensor arranged in the chamber can measure the entire light with a high degree of reproducibility. For this purpose the inner surface of the hollow sphere is provided with a diffusely and highly reflecting white coating or is made from a material with corresponding properties. The light is subjected to multiple reflection by this coating whereby the illumination intensity in the chamber containing the light sensor is homogenized.

In front of the light sensor a diffusion disk may be arranged which prevents light emerging directly from the light outlet portion of the light guide means to be checked from impinging directly onto the light sensor. The spherical chamber thus ensures insensitivity of the measurement with regard to the direction of the light emerging at the optical outlet portion of the light guide means to be checked and with regard to the exact position of the optical outlet portion inside the chamber.

A photodiode is used as light sensor.

In the evaluation means a reference value for the light intensity of the light source can be stored, wherein the evaluation means proportions, as a measure of the transmission losses, the light intensity measured by the light sensor to the reference value, and displays e.g. a percentage value.

The reference value for the light source can also be read into the evaluation means by directly connecting the light source to the opening of the chamber and measuring the reference intensity.

Such an approach is useful e.g. when the light source is replaced by another or a new light source.

Further, reference values for transmission losses for specific endoscopic means to be checked can be stored in the evaluation means such that the evaluation means can display any exceeding of given minimum transmission values.

BRIEF DESCRIPTION OF THE DRAWING

Hereunder an embodiment of the invention is explained in detail with reference to the drawing. The only FIGURE shows the device according to the invention for detecting transmission losses of an endoscopic means by measurements.

DESCRIPTION OF THE PREFERRED EMBODIMENTS

The device for detecting transmission losses of optical light guide means 2 of an endoscope 3 by means of measurements shown in the only FIGURE comprises an evaluation means 14, a light source 6 which is independent of the means 2 to be checked, and a light sensor 10 arranged in a hollow sphere 36.

The evaluation means 14 is provided with a display means 18 for displaying the measurement result, as well as an electronic circuit 16 which comprises on the one hand a constant-current supply unit for a light source 6 consisting of a photodiode, and on the other hand a storage means for reference values for the light source used and for the light guide means to be checked. Further, the electronic circuit 16 comprises an input for the output signal of the at least one light sensor 10, which signal is fed via an amplifier 12 to the electronic circuit 16. The electronic circuit 16 proportions the amplified measuring signal of the light sensor 10 to a predetermined reference value and displays the measurement result on the display means 18. The transmission loss can e.g. be displayed as a percentage value. Thus the user obtains a measure for the transmission loss of the light guide means 2 to be checked. These light guide means 2 consist e.g. of light guide cables or light guide fibers contained in the endoscope. When reference values for transmission losses are stored for specific light guide means 2, it is possible to display the measured transmission loss in relation to a new or reference instrument.

The light guide 6 preferably consists of a light-emitting diode arranged in a connector 28. The connector 28 fits e.g. on the standardized endoscope connection 32 for light guide cables.

The connector 28 further fits on the inlet connection of the light guide cable. Thus it is possible to examine either endoscopes or light guide cables or other light-conducting light guide means, wherein an adapter part for the connection of the light source 6 may be required.

According to the FIGURE, the distal end of the endoscope 3 is introduced through an opening 22 into a chamber 20 of a hollow sphere 36. The opening is suitably sealed against ambient light e.g. by one or a plurality of rubber seals not shown in the FIGURE.

The inner surface 24 of the hollow sphere is provided with a matt white and highly reflecting coating or consists of a matt white highly reflecting material, e.g. Teflon, such that the light emerging from the optical outlet portion 8 at the distal end of the endoscope 3 is diffusely reflected at the inner surface 24 of the hollow sphere 36.

The homogenized light reflected and diffusely scattered in the chamber 20 is measured by the light sensor 10, wherein a diffusion disk 40 can be arranged in front of a light sensor 10 consisting of a photodiode to prevent direct light from the optical outlet portion of the light guide means 2 from being applied to the light sensor 10. This is necessary in particular when e.g. the illumination means of the endoscope 3 generates a wide light cone at the optical outlet portion 8.

The light sensor 10 of the embodiment shown in the only FIGURE is arranged at an 90° angle relative to the opening 22 of the chamber 20. The opening 22 can of course be arranged at an angle of less than 90° relative to the optical axis of the light sensor 10. With the aid of the diffusely reflecting inner surface 24 of the hollow sphere 36 and the diffusion disk 40 the light sensor 10 can perform a measurement with a high degree of reproducibility and accuracy independent of the angle of incidence of the light at the opening 22 and under homogenization of the incident light. With the aid of the evaluation means 14 the transmission loss between the optical inlet portion 4 and the optical outlet portion 8 can then be determined in a simple manner at a minimum expenditure of time.

Although a preferred embodiment of the invention has been specifically illustrated and described herein, it is to be understood that minor variations may be made in the apparatus without departing from the spirit and scope of the invention, as defined by the appended claims.

What is a claimed is:

1. A device for detecting transmission losses of optical light guide means comprising optical light guide means (2) having an optical inlet portion (4) through which light from a separate light source (6) is transmitted to an optical outlet portion (8) of the light guide means (2), at least one light sensor (10) arranged in a chamber (20) for measuring the light intensity emerging from the optical outlet portion (8) of the light guide means (2) to be checked and diffusely reflected in the chamber (20), evaluation means (14) for evaluating the measuring signal from the at least one light sensor (10), the evaluation means (14) having a display means (18) for displaying the measurement result, said optical light guide means (2) is part of an endoscope (3), said optical inlet portion (4) of said light guide means (2) to be checked is located at the optical inlet portion (4) of the light guide means (2) contained in the endoscope (3), said separate light source (6) is independent of the light guide means (2) to be checked contained in said endoscope (3) couples a predetermined light intensity into the optical inlet portion (4) of said endoscope (3), and the optical outlet portion (8) of said endoscope (3) is introduced through an opening (22) of the chamber (20) into the chamber (20).

2. The device as defined in claim 1 wherein the light source (6) consists of a light-emitting diode.

3. The device as defined in claim 2 wherein the light source (6) is arranged in a connector (28) which is adapted to the connection (32) of the optical inlet portion of the light guide means (2) to be checked.

4. The device as defined in claim 1 wherein the light source (6) is arranged in a connector (28) which is adapted to the connection (32) of the optical inlet portion of the light guide means (2) to be checked.

5. The device as defined in claim 1 wherein the chamber (20) comprises a spherical inner surface (24).

6. The device as defined in claim 1 wherein a diffusion disk (40) is arranged in front of the light sensor (10), which diffusion disk (40) scatters the light from the optical outlet portion (8) of the light guide means (2) to be checked which directly impinges onto the light sensor (10).

7. The device as defined in claim 1 wherein the axis of the light emerging from the optical outlet portion (8) of the light guide means (2) to be checked through the opening (22) of the chamber (20) has an angle of $\leq 90°$ relative to the light detection axis of the light sensor (10).

8. The device as defined in claim 1 wherein the light sensor (10) consists of a photodiode.

9. The device as defined in claim 1 wherein a reference value for the light intensity of the light source (6) is stored in the evaluation means (14), and the evaluation means (14) calculates the transmission loss as the quotient of the light intensity value measured by the light sensor (10) and the reference value and displays it as a percentage value on the display means (18).

10. The device as defined in claim 9 wherein the reference value is adapted to be read into the evaluation means (14) by directly connecting the light source (6) to the opening (22) of the chamber (20) and measuring the reference light intensity.

11. The device as defined in claim 10 wherein for predetermined endoscopic light guide means (2) to be checked, minimum transmission values are stored in the evaluation means (14), which minimum transmission values are adapted to be recalled as reference values during the measuring process.

12. The device as defined in claim 9 wherein for predetermined endoscopic light guide means (2) to be checked, minimum transmission values are stored in the evaluation means (14), which minimum transmission values are adapted to be recalled as reference values during the measuring process.

13. The device as defined in claim 1 wherein the chamber (20) is arranged in a hollow sphere (36).

* * * * *